(12) United States Patent
Katzlinger et al.

(10) Patent No.: US 9,892,893 B2
(45) Date of Patent: Feb. 13, 2018

(54) COOLED PHOTOMULTIPLIER TUBE BASED LIGHT DETECTOR WITH REDUCED CONDENSATION, AND RELATED APPARATUSES AND METHODS

(71) Applicant: Molecular Devices, LLC, Sunnyvale, CA (US)

(72) Inventors: Michael Katzlinger, Eugendorf (AT); Bernhard Schinwald, Munderfing (AT); Stefan Auer, Saaldorf-Surheim (DE)

(73) Assignee: Molecular Devices, LLC, Sunnyvale, CA (US)

( * ) Notice: Subject to any disclaimer, the term of this patent is extended or adjusted under 35 U.S.C. 154(b) by 55 days.

(21) Appl. No.: 14/664,953

(22) Filed: Mar. 23, 2015

(65) Prior Publication Data
US 2016/0284525 A1    Sep. 29, 2016

(51) Int. Cl.
*H01J 43/28* (2006.01)
*G01N 21/64* (2006.01)
*G01N 21/15* (2006.01)
*H05K 7/20* (2006.01)

(52) U.S. Cl.
CPC ............ *H01J 43/28* (2013.01); *G01N 21/15* (2013.01); *G01N 21/645* (2013.01); *G01N 21/6452* (2013.01); *G01N 2021/158* (2013.01); *H05K 7/20163* (2013.01)

(58) Field of Classification Search
CPC ............ G01N 2021/158; G01N 21/15; G01N 21/645; G01N 21/6452; H01J 43/28; H05K 7/20163
See application file for complete search history.

(56) References Cited

U.S. PATENT DOCUMENTS

| 2002/0043625 A1* | 4/2002 | Shimizu | G01T 1/208 |
| | | | 250/458.1 |
| 2008/0247038 A1* | 10/2008 | Sasaki | G02B 21/0024 |
| | | | 359/395 |
| 2013/0009053 A1* | 1/2013 | Wu | G01N 27/622 |
| | | | 250/282 |

FOREIGN PATENT DOCUMENTS

| JP | 06088747 A | * | 3/1994 |
| JP | 09145644 A | * | 6/1997 |

OTHER PUBLICATIONS

Machine Translation to English of JP 06088747.*
English Abstract and Japanese text for JP 06088747.*
English Abstract and Japanese text for JP 09145644.*

* cited by examiner

*Primary Examiner* — Francis M Legasse, Jr.

(57) ABSTRACT

A light detector includes a cooling device between a photomultiplier tube (PMT) device and a heat sink. A thermally conductive shield encloses the PMT device and the cooling device and is in thermal contact with the heat sink such that the heat sink transfers heat to the shield. The light detector may be included in sample analyzing apparatus configured for making optical measurements of a sample.

25 Claims, 4 Drawing Sheets

COOLED PHOTOMULTIPLIER TUBE BASED LIGHT DETECTOR WITH REDUCED CONDENSATION, AND RELATED APPARATUSES AND METHODS

TECHNICAL FIELD

This present invention generally relates to a light detector that includes a photomultiplier tube (PMT), and particularly a light detector capable of cooling the PMT while preventing or reducing the development of condensation on the PMT and other components of the light detector.

BACKGROUND

A light detector may utilize a photomultiplier tube (PMT) to detect light, particularly from weak or dim sources of light. The PMT is a vacuum tube that encloses a photocathode, an electron multiplier, and an anode. In accordance with the photoelectric effect, incident photons striking the photocathode cause the photocathode to emit electrons (photoemission). The electrons are multiplied by the electron multiplier, which comprises a series of dynodes. The dynodes cause successive instances of secondary electron emission, ultimately producing enough electrons to generate a useful current that can be correlated to photon counts or intensity. For many optical-based measurement applications, for example fluorescence and luminescence measurement, the PMT may be considered to be the preferred type of light detector component in view of its relatively low cost, high gain, high frequency response, large numerical aperture, and capability for single photon counting.

Optical-based analytical instruments that often utilize PMTs include optical plate readers commonly employed in the life science industry (e.g., for biochemistry, cell biology, immunology, molecular biology, and microbiology). Such instruments typically take measurements from samples in microplates. Such instruments may be configured to perform a specific type of measurement (e.g., fluorescence, luminescence, absorbance, cell imaging, etc.), or may be capable of performing multiple types of measurements at the selection of the user. The latter type of instrument is often termed a "multimode" analytical instrument or multimode reader. Certain multimode readers are configured to receive application-specific cartridges that enable a user to select the type of experiment to be performed on a sample. The selected cartridge is coupled to the instrument whereby the instrument is properly configured for carrying out the selected experiment. The cartridge may contain optics specific to or optimized for a particular type of application. The internal optics housed within the cartridge may communicate with external optics housed within the instrument through optical ports of the cartridge's housing. Some cartridges may additionally include an internal light source and/or light detector. Some examples of cartridge-based multimode readers are described in, for example, U.S. Patent Application Pub. No. 2014/0191138 and U.S. Pat. No. 8,119,066, the entire contents of which are incorporated by reference herein in their entireties.

An optical-based analytical instrument may utilize two different types of PMT to optimize for both fluorescence and luminescence applications. One example is when the fluorescence detection wavelength range needs to go higher than 700 nanometers (nm). In this case a red-sensitive PMT is needed to support the fluorescence wavelength range, and a visible wavelength-only (VIS-only) PMT is needed for luminescence measurement to avoid the higher dark counts or dark current of red-sensitive PMTs. Measuring luminescence with a red-sensitive PMT can limit performance significantly. However, for reasons of cost and/or other reasons, it would be desirable to provide an optical-based analytical instrument that includes a single PMT capable of performing well in different types of experiments. A solution to this problem is to adequately cool a PMT to reduce dark counts or dark current, thereby avoiding the need for a second PMT. Cooled PMTs are commercially available, but are unacceptably large or bulky for integration into a typical optical-based analytical instrument in which space is already limited and for which overall size or footprint is a concern of the user. Moreover, known cooled PMTs often allow condensation to develop on the PMT, which may contaminate the sample under investigation or the sensitive optics and/or electronics of the instrument. Generally, condensation will occur on any cooled surface exposed to moisture-containing air.

Therefore, there is a need for a cooled PMT or PMT-based light detector that is compact and reduces or prevents condensation, and an apparatus or system that includes such a PMT or PMT-based light detector.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a light detector includes: a cooling device comprising a cold side and a hot side and configured for transferring heat from the cold side to the hot side; a photomultiplier tube (PMT) device in thermal contact with the cold side, the PMT device comprising a PMT, an optical input providing an optical path into the PMT, and a bottom side facing the cold side; a heat sink in thermal contact with the hot side; and a thermally conductive shield substantially enclosing the PMT device, the shield comprising an opening through which the optical path passes, wherein the shield is in thermal contact with the heat sink such that the heat sink transfers heat to the shield.

According to another embodiment, a sample analyzing apparatus includes: a light detector according to any of the embodiments disclosed herein; a sample support configured for supporting a sample; and emission optics configured for directing emission light emitted from the sample to the light detector.

According to another embodiment, a method for analyzing a sample includes: introducing a sample into a sample analyzing apparatus; and transmitting emission light emitted from the sample to a light detector according to any of the embodiments disclosed herein.

According to another embodiment, a method for analyzing a sample includes: operating a cooling device of a light detector according to any of the embodiments disclosed herein to cool a photomultiplier tube (PMT), wherein heat is transferred to a shield to prevent condensation on or in the light detector; inducing emission of light from a sample; and transmitting the light emitted from the sample to the light detector.

According to another embodiment, a method for analyzing a sample includes: operating a light detector comprising a photomultiplier tube (PMT); cooling the PMT by transferring heat from the PMT to a heat sink; transferring heat from the heat sink to a thermally conductive shield substantially enclosing the PMT to prevent condensation on or in the PMT; inducing emission of light from a sample; and transmitting the light emitted from the sample through an opening in the shield to the PMT.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
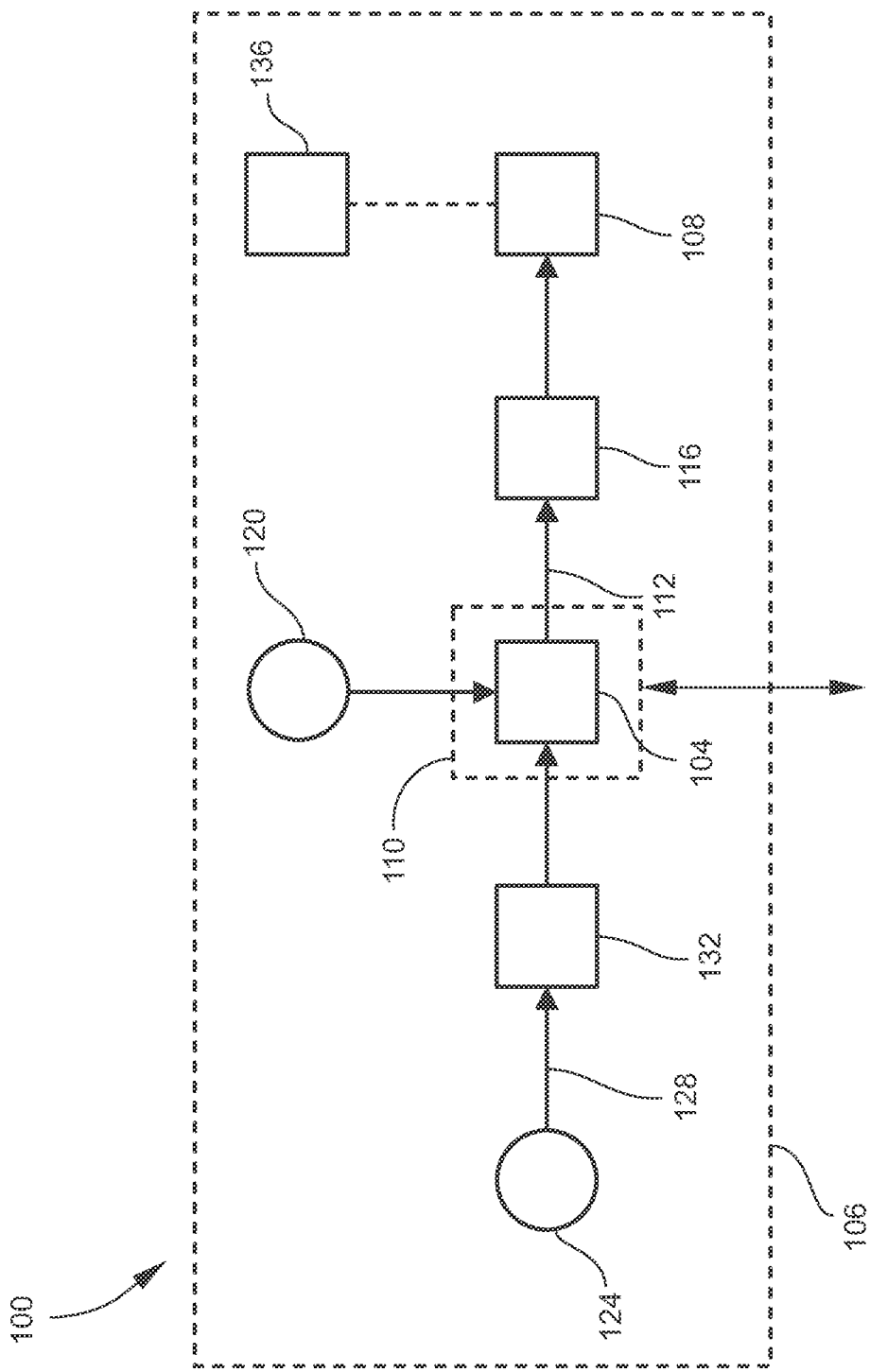
FIG. 1 is a schematic view of an example of a sample analyzing apparatus according to some embodiments.

FIG. 1 is a schematic view of an example of a sample analyzing apparatus or system 100 according to some embodiments. The sample analyzing apparatus 100 is configured for performing an optical measurement on a sample such as, for example, a chemical compound, a biological compound, a biological cell or component(s) thereof, etc. The optical measurement may be based on, for example, luminescence, fluorescence, absorbance, cell imaging, etc. In some embodiments, the sample analyzing apparatus 100 is configured to enable a user to select a desired type of optical measurement to be performed. For example, the user may be able to reconfigure the optics of the sample analyzing apparatus 100 to perform a desired type of luminescence, fluorescence, or absorbance measurement. Thus, in some embodiments the sample analyzing apparatus 100 may be a multi-mode reader. For example, as described above a multi-mode reader may be reconfigurable by enabling a user to select an application-specific cartridge among a number of different cartridges available, and load the selected cartridge into the multi-mode reader so as to establish optical and electrical circuits specific to the desired application. Examples of cartridge-based multi-mode readers are described in above-referenced U.S. Patent Application Pub. No. 2014/0191138 and U.S. Pat. No. 8,119,066. It will be understood that terms such as luminescence, fluorescence, absorbance, cell imaging, and the like generally encompass a variety of optical measurement or imaging techniques related to such terms. For example, the term luminescence may encompass chemiluminescence or bioluminescence. As another example, the term fluorescence may encompass fluorescence intensity (FI), time-resolved fluorescence (TRF), time-resolved fluorescence energy transfer (TR-FRET), fluorescence polarization (FP), etc. Moreover, the sample analyzing apparatus 100 may configured for performing various types of spectroscopy, light scattering measurements, nephelometry, microscopy, etc.

Generally, the structure and operation of the various components provided in optical-based sample analysis instruments are understood by persons skilled in the art, and thus are only briefly described herein to facilitate an understanding of the presently disclosed subject matter. In the illustrated embodiment, the sample analyzing apparatus 100 includes a sample support 104 configured for supporting one or more samples under analysis, and a light detector 108 configured for receiving and measuring emitted light 112 emitted from the sample. The sample support 104 when in an operative position for carrying out optical measurement of the sample, and the light detector 108 and other components illustrated in FIG. 1, may be enclosed in an apparatus housing 106 of the sample analyzing apparatus 100. The apparatus housing 106 may include one or more panels, doors, drawers, etc. for loading the sample support 104 and cartridges if provided, accessing interior regions of the sample analyzing apparatus 100, etc.

Generally, the sample support 104 may be one or more containers configured for holding one or more samples during an analysis. As non-limiting examples, the sample support 104 may be a multi-well plate (also known as a microtiter plate, microplate, or optical plate), one or more cuvettes, etc. The sample support 104 may be disposed on a sample carrier (or sample support carrier) 110 configured for moving the sample support 104 along more or more axes. For example, the sample carrier 110 may be a manually actuated, semi-automated, or motorized stage or platform. The sample carrier 110 may be movable into and out from the apparatus housing 106, as indicated by an arrow in FIG. 1. A sample, or the sample support 104 containing one or more samples, may be mounted onto the sample carrier 110 while the sample carrier 110 is at an outside position, e.g., where the sample carrier 110 is positioned at least partially outside the apparatus housing 106. The sample carrier 110 may thus also be considered as a sample support. The sample carrier 110 may then be moved to an inside position at which the sample carrier 110 is positioned entirely in the apparatus housing 106 so as to align the sample (or successively align multiple samples) with an optical component and/or liquid handling component of the sample analyzing apparatus 100.

In various embodiments, the light detector 108 includes a photomultiplier tube (PMT). As appreciated by persons skilled in the art, a PMT typically includes a series of electrodes enclosed in an evacuated glass tube, for example a photocathode located at the optical input end of the tube, followed by a series of dynodes, and in turn followed by an anode. One or more focusing electrodes may be located between the photocathode and the first dynode. The anode is in signal communication with an electrical connector located at the output end of the glass tube, typically via a sealed electrical feed-through structure. The light detector 108 may also include an outer detector housing that encloses and protects the PMT. Embodiments of the light detector 108 are described further below. The optical input end of the light detector 108 typically includes a lens. The output end may include an electrical connector (e.g., contacts, terminals, pins, wire support, etc.) to provide power and enable measurement signals generated by the light detector 108 to be outputted to signal processing circuitry (e.g., data acquisition circuitry) provided with or external to the sample analyzing apparatus 100.

In typical embodiments, the sample analyzing apparatus 100 further includes emission optics 116 configured for transmitting the emitted light 112 from the sample to the light detector 108. The emission optics 116 may also be configured for processing the emitted light 112. Examples of processing include, but are not limiting to, collecting, focusing, collimating, filtering, beam steering, beam splitting, and optical path switching. Thus, depending on the embodiment, the emission optics 116 may include one or more lenses, read heads, apertures, filters, light guides, mirrors, beam splitters, monochromators, diffraction gratings, prisms, optical path switches, etc. The emission optics 116 may configured for receiving emitted light 112 from above the sample (e.g., a top read head) and/or below the sample (e.g., a bottom read head).

In some embodiments, the sample analyzing apparatus 100 further includes a liquid dispensing system 120 (e.g., injector needle, tubing, pump, etc.) configured for adding a liquid to the sample (e.g., into selected wells of the sample support 104) before or after the sample has been operatively positioned in the sample analyzing apparatus 100. For example, in embodiments measuring luminescence a reagent may be added to the sample to induce luminescence, as appreciated by persons skilled in the art. The reagent may be, for example, a flash luminescence reagent (e.g., aequorin or other photoprotein) or a glow luminescence reagent (e.g., luciferase, luciferin). In some embodiments, two or more different types of reagents may be added. For example, firefly luciferase may first be added followed by *Renilla* luciferase. In some embodiments, the second reagent may include a quenching agent that quenches the signal resulting from the previously added first reagent. As another example, labeling agents may be added for fluorescence or other types of measurements.

In embodiments requiring excitation, the sample analyzing apparatus 100 includes one or more light sources 124 for producing excitation light 128 of a desired wavelength that is directed to the sample. Depending on the embodiment, the light source 124 may include a broadband light source (e.g., flash lamp) or one or more light emitting diodes (LEDs), laser diodes (LDs), etc. Multiple light sources 124 may be provided to enable a user to select a desired excitation wavelength. In typical embodiments, the sample analyzing apparatus 100 further includes excitation optics 132 configured for transmitting the excitation light 128 from the light source 124 to the sample. The excitation optics 132 may include, for example, one or more lenses, read heads, apertures, filters, light guides, mirrors, beam splitters, monochromators, diffraction gratings, prisms, optical path switches, etc., as noted above.

As also schematically illustrated in FIG. 1, the sample analyzing apparatus 100 may further include a computing device (or system controller) 136. As appreciated by persons skilled in the art, the computing device 136 may represent one or more modules configured for controlling, monitoring and/or timing various functional aspects of the sample analyzing apparatus 100, and/or for receiving data or other signals from the sample analyzing apparatus 100 such as measurement signals from the light detector 108 and control signals to the light detector 108. For all such purposes, the computing device 136 may communicate with various components of the sample analyzing apparatus 100 via wired or wireless communication links, as depicted by a dashed line between the computing device 136 and the light detector 108. For simplicity, other communication links that may be present between the computing device 136 and other components of the sample analyzing apparatus 100 are not shown. In typical embodiments, the computing device 136 includes a main electronic processor providing overall control, and may include one or more electronic processors configured for dedicated control operations or specific signal processing tasks. The computing device 136 may also include one or more memories and/or databases for storing data and/or software. The computing device 136 may also include a computer-readable medium 136 that includes instructions for performing any of the methods disclosed herein. The functional modules of the computing device 136 may comprise circuitry or other types of hardware (or firmware), software, or both. For example, the modules may include signal processing (or data acquisition) circuitry for receiving measurement signals from the light detector 108 and software for processing the measurement signals such as for generating graphical data. The computing device 136 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The computing device 136 may include an operating system (e.g., Microsoft Windows® software) for controlling and managing various functions of the computing device 136.

An example of a method for analyzing a sample will now be described. The sample is introduced into the sample analyzing apparatus 100 and placed in a proper operating position relative to optics and other components of the sample analyzing apparatus 100. Generally, the "operating" position of the sample is an "optically aligned" position, i.e., a position that establishes an optical path sufficient for optical data acquisition from the sample. Depending on the experiment, the operating position may also correspond to the sample being "fluidly aligned" with the sample analyzing apparatus 100, i.e., positioned so as to be able to dispense fluid onto the sample such as by operating the liquid dispensing system 120. Sample introduction may entail loading one or more samples in one or more wells of a microplate or other type of sample support 104, and loading or mounting the sample support 104 in the sample analyzing apparatus 100, such as with the use of a sample carrier 110 as noted above. Depending on the sample and the type of measurement to be made, the sample may be subjected to preparation or treatment (incubation, mixing, homogenization, centrifuging, buffering, reagent addition, etc.) prior to being positioned in the sample analyzing apparatus 100, as appreciated by persons skilled in the art.

In addition to sample introduction, depending on design the sample analyzing apparatus 100 or certain components thereof (optics, electronics, etc.) may need to be configured for implementing the specific type of measurement to be made. For example, if cartridge-based, the appropriate cartridge may be installed in the sample analyzing apparatus 100. After installing a cartridge, optics provided in the cartridge become part of the optical circuit within the housing 106 of the sample analyzing apparatus 100. For example, the cartridge optics may be aligned with (in optical communication with) the emission optics 116 and light detector 108, and in some embodiments also with the excitation optics 132 and light source 124. Installing the cartridge results in establishing electrical paths for transmitting power, data and control signals to and/or from the cartridge.

The sample is then processed as necessary to induce the emission of photons from the sample which, depending on the experiment (e.g., luminescence, fluorescence, absorbance, etc.), may entail reagent addition using the liquid dispensing system 120 and/or irradiation/excitation using the light source 124 and associated excitation optics 132. The emission optics 116 collect the emitted light 112 from the sample and direct the emitted light 112 to the light detector 108. The light detector 108 converts these optical signals into electrical signals (detector signals, or measurement signals) and transmits the electrical signals to signal processing circuitry, such as may be provided by a computing device 136 of the sample analyzing apparatus 100 as described above. In the case of multiple samples, the sample support 104 may be moved (such as by using a sample carrier 110 as described above) to sequentially align each additional sample with the optics being utilized for the experiment, whereby measurements are taken from all samples sequentially.

Figure 2:
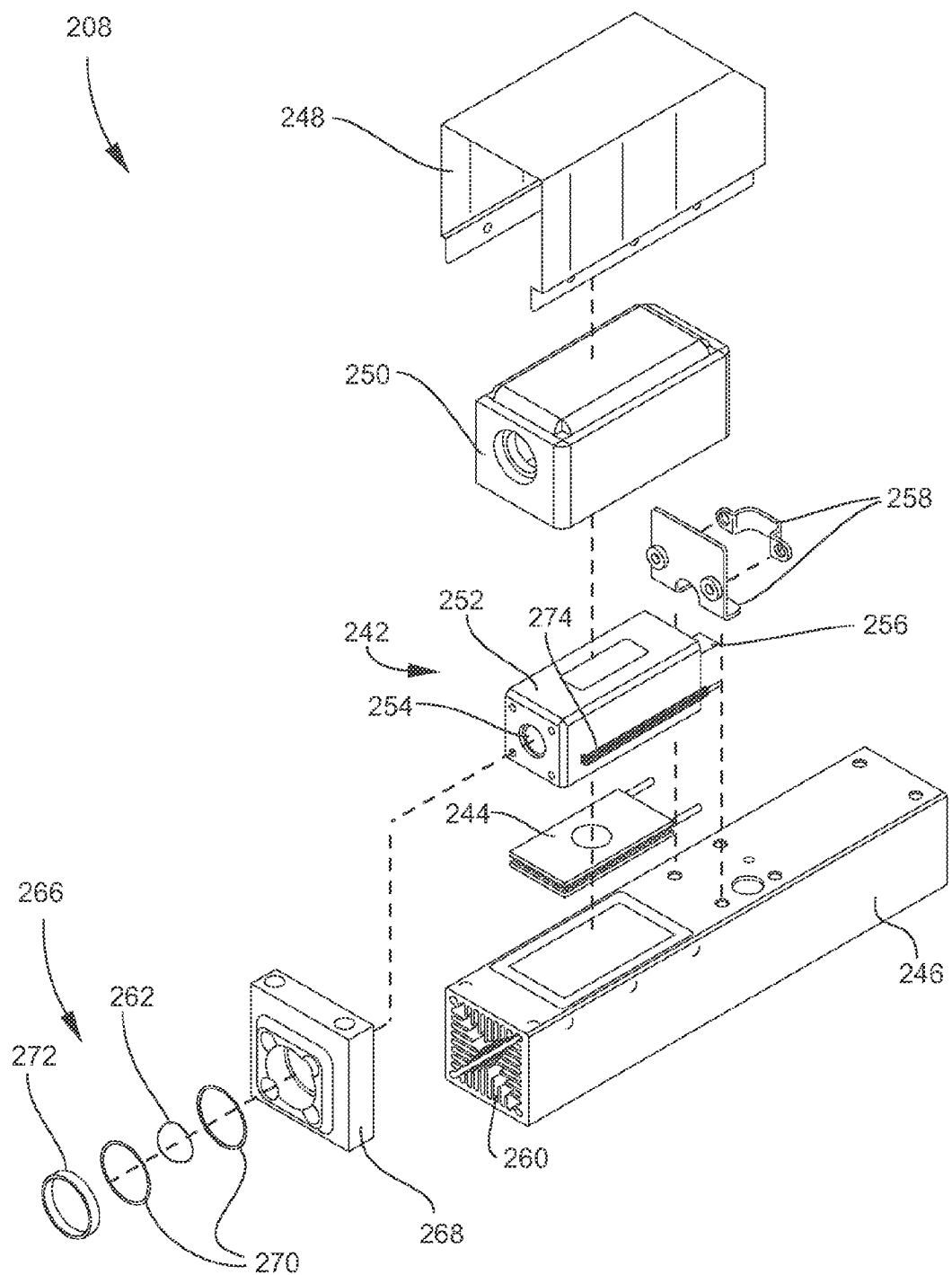
FIG. 2 is an exploded view of an example of a light detector (or light detector assembly) according to some embodiments.
Figure 3:
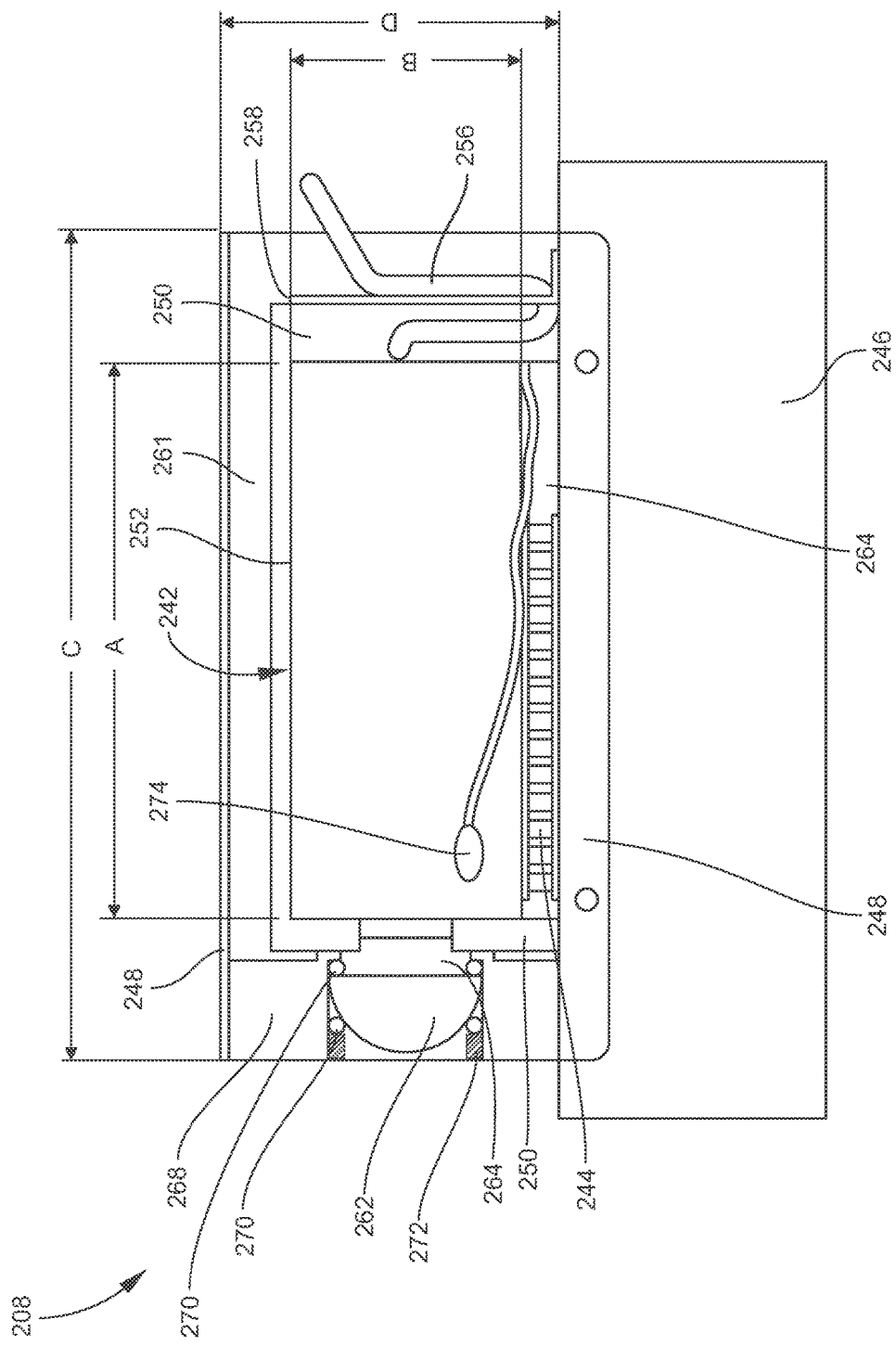
FIG. 3 is a cross-sectional side view of the light detector illustrated in FIG. 2, in assembled form.

FIG. 2 is an exploded view of an example of a light detector (or light detector assembly) 208 according to some embodiments. FIG. 3 is a cross-sectional side view of the light detector 208 in assembled form. The light detector 208 may generally include a PMT device (or PMT module) 242, a thermoelectric (or Peltier) cooling device 244, a heat sink 246, and a thermally conductive shield 248. The cooling device 244 may be positioned between the PMT device 242 and the heat sink 246 such that the PMT device 242 is in thermal contact with the cold side of the cooling device 244 and the heat sink 246 is in thermal contact with the hot side of the cooling device 244. The shield 248 may be in thermal contact with the heat sink 246, as described further below. The light detector 208 may also include a thermal insulation material such as a thermally insulating structure 250 positioned and configured to thermally isolate the PMT device 242, as described further below.

In the context of the present disclosure, two components are in "thermal contact" with each other if one of the components is able to transfer heat to the other component. No intervening thermally insulating barrier (e.g., vacuum barrier or other poorly thermally conductive barrier) exists between the two components to appreciably impair heat exchange between the two components. Typically, the two components in thermal contact with each other are also in spatial proximity to each other. However, no specific limitation is placed on the distance between the two components. The two components in thermal contact with each other may or may not be in physical contact with each other. Thus, depending on the embodiment, the mode of heat transfer may entail convection and/or conduction (as well as radiation).

The PMT device 242 may be configured as described above in conjunction with FIG. 1. The PMT device 242 includes at least the PMT, i.e., the evacuated tube itself. Some embodiments may provide a PMT module that includes an outer detector housing 252 enclosing the evacuated tube of the PMT device 242. The detector housing 252 may be composed of a suitable thermally conductive material (e.g., sheet metal). The detector housing 252 includes an optical input opening 254 for admitting the emission light to be measured. The PMT device 242 may also include a connector cable 256 providing low-voltage power to the PMT device 242 and signal lines to the measurement electronics. The high voltage applied to the PMT tube may be generated by circuitry located inside the detector housing 252. The PMT device 242 may include a cable mount 258 (e.g., one or more brackets) for mounting and positioning the connector cable 256 at the back end of the PMT device 242. The cable mount 258 may be composed of a suitable thermally conductive material (e.g., sheet metal) and positioned in thermal contact with the heat sink 246. For example, the cable mount 258 may be in direct physical contact with the heat sink 246.

For purposes of reference, description, and illustration, the PMT device 242 may be considered as including a front side that is the optical input side (where the optical input opening 254 is located), i.e., the side that receives the light to be measured. The PMT device 242 further includes a back (rear) side opposing the front side, a top (upper) side between the front and back sides, a bottom (lower) side opposing the top side, and two opposing lateral sides between the front and back sides and also between the top and bottom sides. The terms front, back, top, bottom, lateral, and the like are merely relative terms that are consistent with the perspective of FIGS. 2 and 3, but do not limit the PMT device 242 to any particular orientation. Moreover, such terms do not limit the PMT device 242 to any particular shape. The PMT device 242 may generally have any shape. As used herein, the term "side" may be used interchangeably with other terms such as end, surface, wall, or sheet, unless otherwise indicated or the context dictates otherwise. The foregoing applies to any other device or component described herein.

The cooling device 244 may generally be any device that creates a temperature gradient effective for carrying heat away from the PMT device 242. In some embodiments, the cooling device 244 is an active cooling device, particularly an actively controlled cooling device. For example, the cooling device 244 may be a thermoelectric (Peltier) device, which utilizes the thermoelectric effect (or Peltier effect) to create heat flux directed from one side of the device (cold side) to the other side of the device (hot side). For this purpose, the cooling device 244 may have a known thermoelectric device configuration. For example, the cooling device 244 may include an alternating set of p-type and n-type semiconductors positioned thermally in parallel with each other and electrically in series with each other, and positioned between two parallel thermally conducting plates. A thermal gradient from one plate to the other plate is generated by applying a voltage to the free ends of the semiconductors, resulting in direct current (DC) current flow across the junctions of the semiconductors and inducing the thermoelectric effect. In some embodiments, the cooling device 244 may include two or more thermoelectric cooling units operating in concert to provide a cumulative cooling effect. A thermoelectric device is useful in the present embodiment due to its compactness, lack of moving parts, and precise temperature control. However, other embodiments may utilize other types of cooling devices. As shown in the illustrated embodiment, the cold side of the cooling device 244 may be in direct physical contact with the bottom side of the PMT device 242 (e.g., the bottom side of the detector housing 252), and the hot side of the cooling device 244 may be in direct physical contact with the heat sink 246.

The heat sink 246 generally is configured for absorbing the heat dissipated by the hot side of the cooling device 244, and for maintaining other components of the light detector 208 in thermal contact with the heat sink 246 at a temperature warm enough to prevent condensation on such components. For these purposes, in some embodiments and as illustrated, the heat sink 246 may be or include an open duct structure formed by a wall (or walls) composed of a suitable thermally conductive material (e.g., sheet metal). Air flows through the heat sink 246, carrying heat away from the wall(s). The air flow may or may not be aided by a fan or blower. In some embodiments, cooling fins 260 may extend from the wall(s) into the interior of the heat sink 246 to enhance heat transfer by increasing the surface area exposed to the air flow. In some embodiments, the heat sink 246 may be maintained at substantially ambient temperature (e.g., room temperature) at substantially all times during operation of the PMT device 242.

The shield 248 is useful for protecting the PMT device 242 from electromagnetic fields. In addition, the shield 248 is configured (sized, shaped, positioned) to ensure that no cold surface of the light detector 208, particularly the PMT device 242, is exposed to airflow, thus ensuring that no cold surface is prone to condensation. For this purpose, the shield 248 substantially encloses the PMT device 242. In the illustrated example, the shield 248 comprises a solid wall or sheet that fully encloses the PMT device 242 on all sides, except for having an opening at the front side so as not to obstruct the optical path of the emission light into the PMT device 242, an opening or feedthrough (not shown) at the back side to accommodate the connector cable 256 coupled to the PMT device 242, and an opening at the bottom side where the cooling device 244 directly faces the PMT device 242. Thus in the present context, the term "substantially" means that the shield 248 fully encloses the PMT device 242 except where accommodations for the optical path, electrical path(s), and heat transfer path(s) (to the cooling device 244) are needed. The shield 248 may also enclose at least a portion of the cooling device 244. For example, in the present embodiment the shield 248 encloses the lateral sides of the cooling device 244.

The shield 248 may be composed of a suitable thermally conductive material (e.g., sheet metal). The shield 248 is in thermal contact with the heat sink 246, such as by being in direct physical contact with the heat sink 246 as in the illustrated embodiment. For example, in the present embodiment where the cooling device 244 is sandwiched between the PMT device 242 and the heat sink 246, one or both lateral sides of the shield 248 may extend past the lateral sides of the cooling device 244 and into overlapping relation with one or more corresponding lateral sides of the heat sink 246. Direct contact may be enhanced by fastening or adhering the lateral side(s) of the shield 248 to the heat sink 246 such as by using screws. By such configurations, the shield 248 thermally isolates the PMT device 242, and the warm heat sink 246 keeps the shield 248 warm thereby preventing condensation on the shield 248. In this manner all cooled components of the light detector 208, including components that are indirectly cooled by being mounted at or in close proximity to the PMT device 242, are heated up to at least ambient temperature. This provides a solution to cooling the PMT device 242 while preventing condensation. Moreover, the solution is achieved while enabling the light detector 208 to remain compact, which is advantageous for the sample analyzing apparatus 100. As shown in FIGS. 2 and 3, the envelope or form factor of the light detector 208 (i.e., the overall space occupied by the light detector 208) may be defined by the outermost dimensions of the shield 248 and the heat sink 246. In some embodiments, the shield 248 has a maximum dimension in any direction (e.g., length, width, height) of about 200 millimeters (mm) or less, or in another embodiment 150 mm or less, or in another embodiment 100 mm or less. As one non-limiting example, referring to FIG. 3 the PMT device 242 may have a length A of 50 mm and a height B of 22 mm. In this example, the shield 248 may have a length C of 80 mm and a height D of 35 mm, with the length C being the maximum dimension in this example.

In some embodiments, the light detector 208 may include insulation material that further thermally isolates the PMT device 242 and prevents condensation but does not increase the envelope established by the shield 248 and the heat sink 246. For example, in the illustrated embodiment the light detector 208 includes a thermally insulating structure 250. The insulating structure 250 is shaped so as to cover all sides of the PMT device 242 except for the bottom side that is directly exposed to the cooling device 244. Thus, in this embodiment the insulating structure 250 is positioned generally between the PMT device 242 and the shield 248. The insulating structure 250 includes an optical input opening aligned with the optical input opening 254 of the detector housing 252 for admitting emission light to be measured by the PMT device 242. In some embodiments, the optical input opening of the insulating structure 250 may be configured for holding a lens, light guide, or other optics component. The insulating structure 250 may be composed of any suitable insulating material such as, for example, a soft foam material (e.g., a suitable thermally insulating polymer having an open-cell structure). The insulating structure 250 may be considered as substantially enclosing the PMT device 242 in a manner similar to that described above in regard to the shield 248.

In some embodiments, the light detector 208 may include another type of insulation material. For example, in the illustrated embodiment a layer or structure composed of sealing glue 260 (FIG. 3) is added so as to encapsulate the PMT device 242, or both the PMT device 242 and the insulating structure 250 if provided. Thus, in this embodiment the sealing glue 260 is positioned generally between the PMT device 242 and the shield 248, or between the insulating structure 250 (if provided) and the shield 248. The sealing glue 260 may provide alternative or additional protection of the interior of the PMT device 242 from ambient conditions. Thus, in some embodiments the light detector 208 may include insulation material such as the insulating structure 250 or sealing glue 260, while in other embodiments the light detector 208 may include a first insulation material (e.g., insulating structure 250) and a second insulation material (e.g., sealing glue 260).

The light detector 208 may further include an optical input lens 262 configured to direct the light to be measured to the photocathode of the PMT device 242. For this purpose, the optical input lens 262 is positioned in alignment with the opening(s) leading into the interior of the PMT device 242. The optical input lens 262 may be spaced from the front end of the PMT device 242 by an air gap 264 (FIG. 3). The optical input lens 262 may be fixed in position by an optical input assembly 266. The optical input assembly 266 may include a lens holder 268 having a through-bore in which the optical input lens 262 is mounted. In the illustrated example, the optical input lens 262 is mounted between two o-ring seals 270 and its position is secured by a retainer ring 272. The lens holder 268 may be composed of a suitable thermally conductive material (e.g., sheet metal) and positioned in thermal contact with the heat sink 246, for example by direct physical contact. By this configuration, the lens holder 268 may be kept warm to prevent condensation.

The light detector 208 may further include a temperature sensor 274 for monitoring the temperature of the PMT device 242. For example, the temperature sensor 274 may be mounted on the outer detector housing 252. The temperature sensor 274 may be provided to control the cooling of the PMT device 242 by outputting a feedback (temperature measurement) signal to a temperature controller (e.g., a temperature control circuit), such as may be part of the above-described computing device 136 (FIG. 1). Based on the temperature measurement signal(s) received, the temperature control circuit may then determine the input voltage or current to apply to the cooling device 244, such as by comparing the measured temperature to a pre-determined set point temperature, utilizing known logic circuitry, etc. The temperature control circuit may then send an appropriate control signal to a power source communicating with the cooling device 244.

Figure 4:
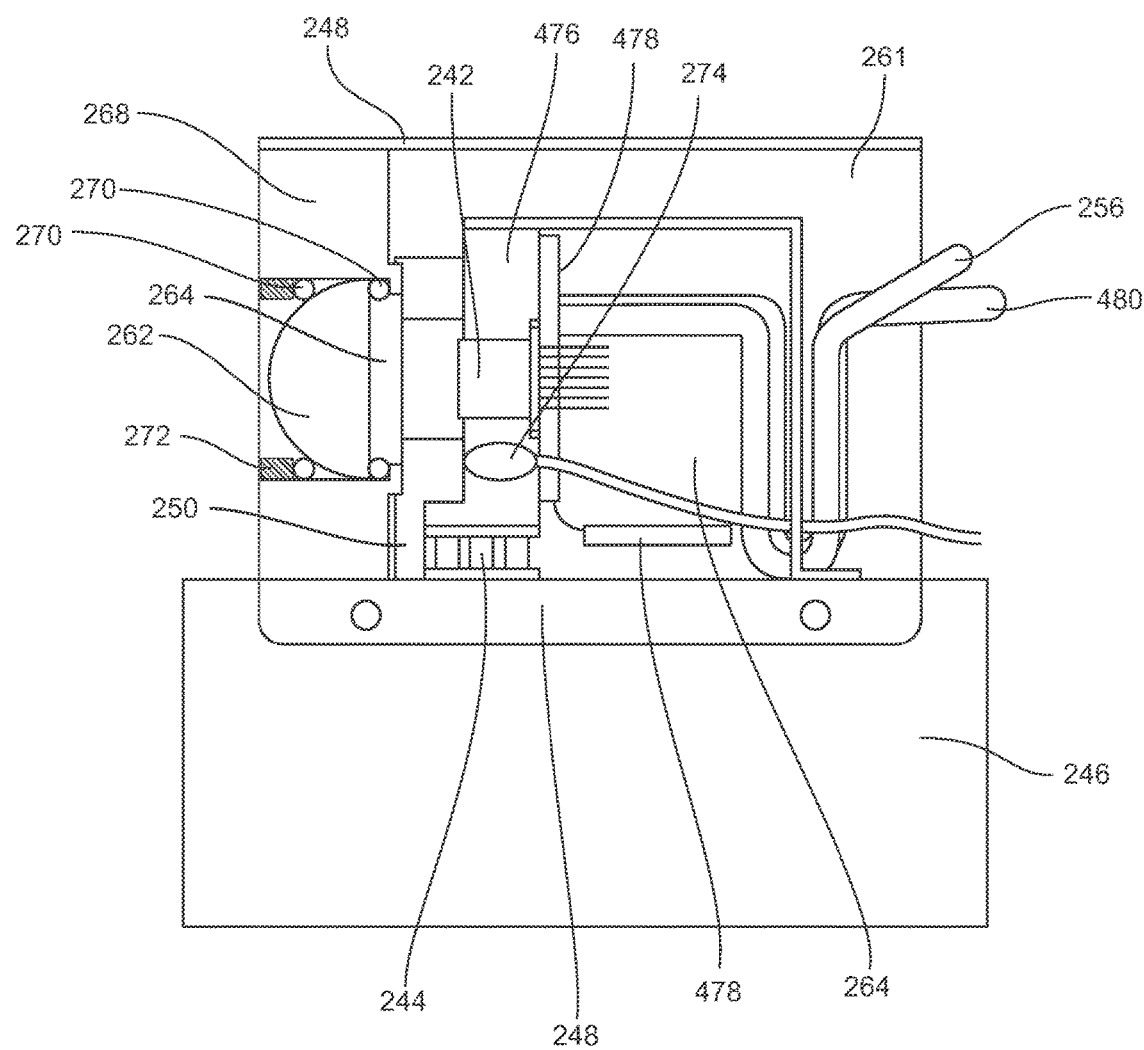
FIG. 4 is a cross-sectional side view of an example of a light detector (or light detector assembly) according to another embodiment.

FIG. 4 is a cross-sectional side view of an example of a light detector (or light detector assembly) 408 according to another embodiment. Many of the components or features of the light detector 408 may be the same as or similar to the light detector 208 described above and illustrated in FIGS. 2 and 3. Accordingly, such components or features are designated in FIG. 4 by the same reference numerals employed in FIGS. 2 and 3, and the description of such components or features is not repeated.

In FIG. 4, the tube of the PMT device 242 is not enclosed in an outer detector housing but instead is mounted in a PMT holder 476 of the PMT device 242. The PMT holder 476 may be composed of a suitable thermally conductive material such as a metal. The PMT device 242 is in thermal contact with the cold side of the cooling device 244 via the bottom side of the PMT holder 476. The PMT holder 476 may be in direct physical contact with the cooling device 244, as illustrated. Also in this embodiment, the dynodes of the PMT device 242 are coupled to circuitry on suitable substrate 478 through, for example, connector pins. The substrate 478 may be, for example, a printed circuit board (PCB) or printed circuit board assembly (PCBA). The low-voltage cable 256 and a high-voltage cable 408 may be connected the substrate 478 to provide the appropriate voltage to the PMT device 242.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the computing device 136 schematically depicted in FIG. 1. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the computing device 136 in FIG. 1), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:
1. A light detector, comprising:
 a cooling device comprising a cold side and a hot side and configured for transferring heat from the cold side to the hot side;
 a photomultiplier tube (PMT) device in thermal contact with the cold side, the PMT device comprising a PMT, an optical input providing an optical path into the PMT, and an outer housing enclosing the PMT, the outer housing comprising a bottom side facing the cold side;
a heat sink in thermal contact with the hot side; and
a thermally conductive shield substantially enclosing the PMT device, the shield comprising an opening through which the optical path passes, wherein the shield is in thermal contact with the heat sink such that the heat sink transfers heat to the shield,
wherein the heat sink comprises a wall forming a duct having an interior, the duct defines a path for air to flow through the interior, and the wall is structurally separate from the outer housing and the shield, and
wherein the shield is connected to the wall forming the duct of the heat sink such that the heat transferred by the cooling device to the hot side is transmitted to the wall of the heat sink to heat the shield substantially enclosing the PMT device.

2. The light detector of claim 1, wherein the cooling device is a thermoelectric cooling device.

3. The light detector of claim 1, wherein the bottom side is in direct contact with the cold side.

4. The light detector of claim 1, wherein the shield is in direct contact with the wall of the duct of the heat sink.

5. The light detector of claim 1, wherein the shield has a maximum dimension of about 200 millimeters or less.

6. The light detector of claim 1, wherein the cooling device is positioned between the PMT device and the heat sink, and the shield encloses at least a portion of the cooling device.

7. The light detector of claim 1, comprising a thermal insulation material positioned between the PMT device and the shield.

8. The light detector of claim 1, comprising an optical input assembly and an optical input lens positioned by the optical input assembly in optical alignment with the optical input of the PMT.

9. The light detector of claim 1, comprising a temperature sensor configured for measuring a temperature of the PMT.

10. A sample analyzing apparatus, comprising:
the light detector of claim 1;
a sample support configured for supporting a sample; and
emission optics configured for directing emission light emitted from the sample to the light detector.

11. A method for analyzing a sample, the method comprising:
operating the cooling device of the light detector of claim 1 to cool the PMT, wherein heat is transferred to the shield to prevent condensation on or in the light detector;
inducing emission of light from a sample; and
transmitting the light emitted from the sample to the light detector.

12. The light detector of claim 7, wherein the thermal insulation material substantially encloses the PMT and comprises an opening through which the optical path passes.

13. The light detector of claim 7, wherein the thermal insulation material comprises foam, or sealing glue, or both foam and sealing glue.

14. The light detector of claim 7, wherein the thermal insulation material comprises a first insulation material positioned between the PMT and the shield, and a second insulation material positioned between the first insulation material and the shield.

15. The light detector of claim 8, wherein the optical input assembly is in thermal contact with the heat sink.

16. The sample analyzing apparatus of claim 10, comprising a light source configured for generating excitation light, and excitation optics configured for directing the excitation light to the sample.

17. The sample analyzing apparatus of claim 10, comprising a temperature controller configured for receiving a temperature measurement signal from the light detector and controlling the cooling device based on the temperature measurement signal.

18. The method of claim 11, comprising controlling heat transfer from the PMT to the cooling device by applying electrical power to the cooling device.

19. The method of claim 18, comprising measuring a temperature of the PMT, wherein controlling heat transfer is based on the measured temperature.

20. The method of claim 11, wherein inducing emission comprises adding a reagent to the sample, or irradiating the sample with excitation light, or both of the foregoing.

21. The method of claim 11, wherein operating the cooling device, inducing emission, and transmitting the light are done in a sample analyzing apparatus in which the sample and the light detector are positioned.

22. The method of claim 21, comprising introducing the sample into the sample analyzing apparatus.

23. A method for analyzing a sample, the method comprising:
operating a light detector comprising a photomultiplier tube (PMT) device, the PMT device comprising a PMT and an outer housing enclosing the PMT, the outer housing comprising an optical input providing an optical path into the PMT;
cooling the PMT by transferring heat from the PMT to a heat sink, the heat sink comprising a wall forming a duct having an interior, the wall being structurally separate from the outer housing and from a thermally conductive shield substantially enclosing the PMT device;
transferring heat from the heat sink to a thermally conductive shield substantially enclosing the PMT to prevent condensation on or in the PMT, wherein the shield is connected to the wall forming the duct of the heat sink such that the heat transferred from the heat sink is transmitted to the wall of the heat sink to heat the shield substantially enclosing the PMT device;
flowing air through the interior of the duct;
inducing emission of light from a sample; and
transmitting the light emitted from the sample through an opening in the shield to the PMT.

24. The method of claim 23, wherein cooling the PMT comprises operating a cooling device positioned between the PMT and the heat sink.

25. The method of claim 23, wherein a thermal insulation material is positioned between the PMT and the shield.

* * * * *